(12) United States Patent
Colloca

(10) Patent No.: US 6,890,528 B1
(45) Date of Patent: May 10, 2005

(54) CELLS FOR THE PRODUCTION OF HELPER DEPENDENT ADENOVIRAL VECTORS

(75) Inventor: Stefano Colloca, Rome (IT)

(73) Assignee: Istituto di Ricerche di Biologia Molecolare P. Angeletti S.p.A., Rome (IT)

(*) Notice: Subject to any disclaimer, the term of this patent is extended or adjusted under 35 U.S.C. 154(b) by 0 days.

(21) Appl. No.: 09/831,182

(22) PCT Filed: Nov. 8, 1999

(86) PCT No.: PCT/IT99/00356

§ 371 (c)(1),
(2), (4) Date: Jul. 18, 2001

(87) PCT Pub. No.: WO00/28060

PCT Pub. Date: May 18, 2000

(30) Foreign Application Priority Data

Nov. 6, 1998 (IT) .................................... RM98A0694

(51) Int. Cl.⁷ ............................................. A01N 63/00
(52) U.S. Cl. .................. 424/93.21; 424/93.2; 424/93.6; 424/233.1; 435/5; 435/69.1; 435/70.1; 435/320.1; 435/325; 435/455; 435/476
(58) Field of Search .............................. 424/93.2, 93.6, 424/233.1, 93.21; 435/5, 69.1, 69.7, 91.2, 235.1, 320.1, 325, 455, 456, 457, 462, 465, 475, 70.1, 476

(56) References Cited

U.S. PATENT DOCUMENTS 5,948,675 A 9/1999 Klatzmann et al.

FOREIGN PATENT DOCUMENTS

| FR | 2 738 575 | 3/1997 |
|---|---|---|
| WO | WO95/22617 | 8/1995 |
| WO | WO97/32481 | 9/1997 |
| WO | 98/13499 | 4/1998 |
| WO | 98/13510 | 4/1998 |
| WO | 00/12740 | 3/2000 |

OTHER PUBLICATIONS

Alemany et al. Complementation of helper–dependent adenoviral vectors:size effects and titer fluctuations. Journal of Virological Methods (1997) vol. 68, pp. 147–159.*
Yeh et al. Efficient dual transcomplementation of adenovirus E1 and E4 regions from 293–derived cell line expressing a minimal E4 functional unit. Journal of Virology (1996) vol. 70, No. 1, pp. 559–565.*
GeneBank # AF083132; M73260; J01917.*
Tuboly et al. Restriction endonuclease analysis and physical mapping of the genome of porcine adenovirus type 5. Virus Research (1995) vol. 37, No. 1, pp. 49–54.*

Baron, U. et al. "Co–regulation of two gene activities by tetracycline via a bidirectional promoter", Nucleic Acids Research, 1995, vol. 23, pp. 3605–3606.
Brough, D. et al. "A Gene Tranfer Vector–Cell Line System for Complete Functional Complementation of Adenovirus Early Regions E1 and E4", Journal of Virology, 1996, vol. 70, pp. 6497–6501.
Bett, A. et al. "An efficient and flexible system for construction of adenovirus vectors with insertions or deletions in early regions 1 and 3", Proc. Natl. Sci. USA, 1994, vol. 91, pp. 8802–8806.
Calos, M. "The potential of extrachromosomal replicating vectros for gene therapy", TIG, 1996, vol. 12, pp. 463–466.
Calos, M. "Stability without a centromere". Proc. Natl. Acad. Sci. USA, 1998, vol. 95, pp. 4084–4085.
Deuschle, U. et al. "Tetracycline–Reversible Silencing of Eukaryotic Promoters", Molecular and Cellular Biology, 1995, vol. 15, pp. 1907–1914.
Engelhardt, J. et al. "Ablation of *E2A* in recombinant adenoviruses improves transgene persistence and decreases inflammatory response in mouse liver", Proc. Natl. Acad. Sci. USA, 1994, vol. 91, pp. 6196–6200.
Freundlieb, S. et al. "A Tetracycline Controlled Activation/Repression System with Increased Potential for Gene Transfer into Mammalian Cells", The Journal of Gene Medicine, 1999, vol. 1, pp. 4–12.
Gossen, M. et al. "Transcriptional Activation by Tetracyclines in Mammalian Cells", Science, 1995, vol. 268, pp. 1766–1769.
Hitt, M. et al. "Techniques for Human Adenovirus Vector Construction and Characterization", Methods in Molecular Genetics, 1995, vol. 7, pp. 13–30.
Hitt, M. et al. "Human Adenovirus Vectors for Gene Tranfer into Mammalian Cells", Advances in Pharmacology, 1997, vol. 40, pp. 137–206.
Kozarsky, K. et al. "*In Vivo* Correction of Low Density Lipoprotein Receptor Deficiency in the Wantanabe Heritable Hyperlipidemic Rabbit with Recombinant Adenoviruses", The Journal of Biological Chemistry, 1994, vol. 269, pp. 13695–13702.

(Continued)

*Primary Examiner*—Ulrike Winkler
(74) *Attorney, Agent, or Firm*—Laura M. Ginkel; Jack L. Tribble

(57) ABSTRACT

The present invention relates to cells for the production of helper dependent adenoviral vectors, including at least the following genic units: a first genic unit comprising an adenovirus defective genome having the inverted terminal repeats in head-to-tail configuration, the encapsidation signal inactivated, and at least one of the non-structural regions inactivated; a second genic unit comprising at least one inducible promoter and at least one of the regions inactivated in the first genic unit, said regions being under the control of said inducible promoter; whereby following the activation of the inducible promoter of the second genic unit and the infection of the cells with said helper dependent adenoviral vectors, the first genic unit and the second genic unit enable the production of said helper dependent adenoviral vectors in said cells in absence of helper vector.

22 Claims, 2 Drawing Sheets

OTHER PUBLICATIONS

Krougliak, V. et al. "Development of Cell Lines Capable of Complementing E1, E4, and Protein IX Defective Adenovirus Type 5 Mutants", Human Gene Therapy, 1995, vol. 6, pp. 1575–1586.

No, D. et al. "Ecdysone–inducible gene expression in mammalian cells and transgenic mice", Proc. Natl. Acad. Sci. USA, 1996, vol. 93, pp. 3346–3351.

Parks, R. et al. "A helper–dependent adenovirus vector system: Removal of helper virus by Cre–mediated excision of the viral packaging signal", Proc. Natl. Acad. Sci. USA, 1996, vol. 93, pp. 13565–13570.

Spencer, D. et al. "Conrolling Signal Transduction with Synthetic Ligands", Science, 1993, vol. 262, pp. 1019–1024.

Wang, Y. et al. "A regulatory system for use in gene transfer", Proc. Natl. Acad. Sci. USA, 1994, vol. 91, pp. 8180–8184.

Yang, Y. et al. "Cellular immunity to viral antigens limits E1–deleted adenoviruses for gene therapy", Proc. Natl. Acad. Sci. USA, 1994, vol. 91, pp. 4407–4411.

Amalfitano, A. et al. "Production and Characterization of Improved Adenovirus Vectros with the E1, E2b, and E3 Genes Deleted", Journal of Virology, 1998, vol. 72, pp. 926–933.

Dedieu, J. et al. "Long–Term Gene Delivery into the Livers of Immunocompetent Mice with E1/E4–Defective Adenoviruses", Journal of Virology, 1997, vol. 71, pp. 4626–4637.

Gorziglia, M. et al. "Elimination of both E1 and E2a from Adenovirus Vectors Further Improves Prospects for In Vivo Human Gene Therapy", Journal of Virology, 1996, vol. 70, pp. 4173–4178.

Gao, G. et al. "Biology of Adenovirus Vectors with E1 and E4 Deletions for Liver–Directed Gene Therapy", Journal of Virology, 1996, vol. 70, pp. 8934–8943.

Recchia, A. et al. "Site–specific integration mediated by a hybrid adenovirus/adeno–associated virus vector", Proc. Natl. Acad. Sci. USA, 1999, vol. 96, pp. 2615–2620.

Rittner, K. et al. "Conditional Repression of the E2 Transcription Unit in E1–E3–Deleted Adenovirus Vectos is Correlated with a Strong Reduction in Viral DNA Replication and Late Gene Expression In Vitro", Journal of Virology, 1997, vol. 71, pp. 3307–3311.

Zhang, Y et al. "A new logic for DNA engineering using recombination in *Escherichia coli*", Nature Genetics, 1998, vol. 20, pp. 123–128.

* cited by examiner

CELLS FOR THE PRODUCTION OF HELPER DEPENDENT ADENOVIRAL VECTORS

This application is the §371 national phase application of PCT International Application no. PCT/IT99/00356, filed 8 Nov. 1999, which claims, under § 119(a), benefit of Italian Application RM98A000694, filed 6 Nov. 1998.

BACKGROUND OF THE INVENTION

An important aspect in the development of gene therapy is the development of vectors capable of introducing genetic material into the target cells. In order to be effective, those vectors are required to possess several features: they must be capable of accommodating large or multiple transgenes inclusive of gene regulation elements, yet remaining simple to manipulate, such as to enable the production thereof on a pharmaceutical scale. Moreover, it is essential that they be safe and of a low toxicity, though preserving the capability of introducing the transgenes in an efficient and selective manner into the target tissues. Finally, the vector should preferably be compatible with an appropriate retention, expression and regulation of the transgene into the target cell.

At present, the adenovirus-based viral vectors seem to be the ones most suitable for manipulations making them capable of meeting all of those requirements. To date they are considered the most effective system for the introduction of heterologous genes in mammalian cells, both in vivo and in cells cultivated in vitro (Hitt M. M. et al.1997. Advances in Pharmacol.40, 137–206).

This is due to some interesting characteristics of the Adenoviruses (Ad), which constitute a DNA virus family (the ones infecting human beings have been classified in 57 serotypes), characterized by an icosahedral capsid lacking an outer coat: they are highly infective but relatively innocuous, primarily infect epithelial cells but can also infect cells of other tissues, regardless of their being in active replication phase. Because of their high infectiousness in vitro of cell lines of human origin, they can easily be produced in large amounts. Moreover, it has been proved that human DNA inserts can be efficiently transferred into epithelial human cells through Ad infection (Horvitz, "Adenoviridae and their replication" in Virology, Field and Knipe, ed. Raven Press, NY; 1990; pages 1679–1740).

With regard to molecular biology of the virus, adenovirus, in particular the human one, has a linear double-stranded DNA genome, of about 36 kb, functionally subdivided into two regions, non-structural and structural. The first one includes regions encoding polypeptides expressed in the first stages of the infection, i.e., prior to the viral DNA replication (E regions), the second ones includes regions coding for polypeptides expressed in the subsequent stages of the viral cycle (L region). Following the infection of a competent cell, when the viral DNA reaches the nucleus, the first region to be transcribed is the E1a region coding for proteins involved in the transactivation of the other regions, both E and L, of the viral DNA. The subsequently transcribed E1b region encodes proteins regulating the RNA synthesis, both viral and of the host cell, and protecting the latter from the apoptotic effect otherwise exerted by E1a. Therefore, the E1a/E1b functions are essential for the viral replication.

The E2 region encodes proteins directly involved in the viral replication, like the viral DNA-polymerase, the pre-terminal protein and proteins binding to the viral DNA. The E3 region encodes proteins that are unnecessary for the viral replication in cultured cells, but are involved, in vivo, in the regulation of the antiviral immune response. Lastly, the E4 region contains groups of genes whose products reduce the gene expression of the host cell and increase the transcription of the E2 and L regions of the viral genome.

The L region of the viral genome essentially encodes proteins of structural type, or anyway involved in the assembling of the viral particles.

In the 40 years following the first isolation, following the characterization of Ad viruses, the relevant modifications that made them efficient carriers for the transfer of genic material have been progressively developed.

In particular the interventions on the Ad genome have been firstly carried out in order to
- increase the capability of the viral genome to accept the insertion of heterologous genes;
- eliminate intracellular toxicity deriving from the expression of adenovirus genes.

Such interventions consist mainly in the provision of progressive deletions of viral regions, whose functions are provided in trans.

In a first generation vectors (derived from human Ad serotypes 2 and 5), the deletion has involved the E1 region, making the virus defective for the capability of replication, unless the proteins produced by such transcriptional unit are provided in trans.

An increase of the size of the heterologous gene to be inserted and the restriction of the propagation of the recombinant viruses in cell lines that complement such defect because they constitutionally express genes of the viral E1 region, have been obtained.

However, the deletion of E1 is not sufficient per se to completely eliminate the expression of other genes of the E and L regions, and to prevent the viral DNA replication. It follows that in animals infected with those vectors the presence of viral antigens and the onset of immune responses aiming at the destruction of the infected cells are detected (Yang et al. Proc. Natl. Acad. Sci. 91:4407–4411; 1994). This leads to the loss of the gene of therapeutic interest and to the onset of inflammatory reactions. Moreover, the persistence of an immunological memory of these reactions can greatly diminish the effectiveness of a second administration of an adenoviral vector of this type (Kozarsky et al. J. Biol; Chem. 269:1–8; 1994).

Hence new, second generation, adenoviral vectors carrying different combinations of early gene deletion have been constructed to improve the safety profile of Adenoviral vectors. Vectors differently combining E1, E2, E3, and/or E4 deletions have been demonstrated to be less cytotoxic in vitro and more stable in mouse liver than the classic ΔE1 first generation vectors (Gao, G-P. 1996 J. Virol 70:8934–8943; Dedieu, J-F. 1997 J. Virol. 71:4626–4637; Gorziglia, M.I. 1996 J. Virol. 70:4173–4178; Amalfitano, A. 1998 J. Virol. 72:926–933). In vivo experiments demonstrated that such deletions effectively diminished, but not abolished, the toxicity.

In addition, vectors carrying additional deletions further increasing the capability of the viral genome to accept the insertion of heterologous genes have been produced (Englehardt et al. Proc. Natl. Acad. Sci. 91:6196–6200; 1994; Bett et al. Proc. Natl. Acad. Sci. 91:8802–8806; 1994; Yeh, P., et al. 1996 J. Virol. 70:559–565). However, the maximum capacity of a first generation adenoviral vector does not exceed 8 kb, whereas that of a ΔE1/E3/E4 vector reaches 11 kb and the foreign genes can be equally inserted in the region E1 or E3.

In this context, following the discovery that a minimal portion, about 600 bp, of the viral DNA is strictly necessary for the replication and the encapsidation of recombinant vectors, totally defective adenoviral vectors, and consequently totally depending on the presence of helper viruses for the replication and the assembling thereof in viral particles, have been developed.

Such kind of helper-dependent adenoviral vectors (ADHD) carry minimal Ad sequences containing the Signals sufficient for the replication and the encapsidation. All the other factors necessary for virion production are provided in trans by a helper virus. The helper genome is constructed in such a manner that its sequences containing encapsidation signals can be easily eliminated in vivo through the use of specific recombination systems like the cre/lox system (WO97/32481).

Accordingly, the relevant strategies for the preparation of helper-dependent Adenovirus virions (adenoHD) are essentially based on the use of three elements:
- cell lines transformed so as to make them capable of expressing the genes encoding the group of adenovirus E1 proteins, and a recombinase, usually "cre";
- a helper adenovirus wherein the E1 region is deleted and wherein the viral DNA sequences required for the encapsidation thereof inside the mature virion are flanked by recombination sites acting as substrates for the recombinase ("loxP" in case of "cre");
- the adenoHD vector carrying the transgene of interest.

Although representing a remarkable improvement over the strategies utilising first generation vectors, this strategy presents some problems. For a production on a pharmaceutical scale, the requirement of controlling three independent components (the cell line, the helper and the transgenic vector) entails difficulties that are hard to overcome and unacceptable production costs.

Firstly, the cre-type recombinases catalyze both the deletion and the insertion of the DNA regions flanked by the loxP sites. The excision reaction is normally up to 20-fold more efficient than the opposite one, however a complete removal of the helper from the viral production can never be obtained. This is unacceptable especially in the pharmaceutical practice, and helper contamination of preparations of therapeutical use is a really serious problem.

A second limitation of this type of strategy is due to the difficulty of optimising the quantitative ratios between helper virus and helper-dependent virus during the amplification process. Hence, the vector amplification seldom approaches the efficiency of first generation vectors, and more often yields lesser to the extent of one order of magnitude are obtained. As in the previous case, this problem is dramatic when a production on an industrial scale is required, the costs becoming practically prohibitive.

In order to solve the problem deriving from the helper virus contamination and to reduce the number of components, an alternative strategy known in the art is that of engineering cell lines to make them capable of expressing all the factors necessary for the encapsidation of the defective virus, eliminating hence the helper virus.

In prior art there are several descriptions of cells expressing one or more viral proteins (see for instance WO98/13499). Such cell lines can be used for the production of adenoviral vectors defective of the complementary viral proteins. However, according to this strategy, it is extremely difficult to satisfactorily produce the exact co-ordination of the events between the viral DNA replication and the expression of the structural proteins that in the natural infection lead to the massive production of viral particles typical of the lytic phase. Accordingly, adopting these strategies, the viral cell cycle cannot be mimicked. In absence of this, only a limited yielding capacity may be achieved.

SUMMARY OF THE INVENTION

Object of the present invention is a helper cell line enabling the production of helper dependent adenoviral vectors in total absence of any kind of helper virus. Such a cell line has been in fact constructed in order to make all the essential functions for the Ad virus replication to be contained in the cells, splitted in particular in two genic units allowing a strictly regulated expression thereof.

The first genic unit comprises at least one defective Ad genome having the Inverted Terminal Repeats (ITRs) in head-to-tail configuration, and having the encapsidation signal and at least one of the non-structural regions inactivated.

Such non-structural regions can be expressed to regions, or cys-acting elements. The expressed regions can be both not-translated non-structural genes, like for instance the VA ones, or translated non-structural genes like the E1, E2 and E4 genes.

In a preferred embodiment the inactivation is carried out by totally, or more preferably by partially, deleting at least one of such regions; the encapsidation signal as well is preferably inactivated by total or partial deletion.

Such a first genic unit can be located on an episomal unit or can be integrated in the genome of the host cells.

In the first case, the episomal unit must comprise at least one element enabling the replication of the episomal unit itself at a low number of copies. Such element can be constituted by sequences mediating DNA replication and its retention in the nucleus (Calos MP. 1996 Trends Genet 12: 463–466), or by the origin of replication of the origin of replication system of a virus, activated by at least one activating factor.

The origin of replication must be in any case located on the episomal unit; the activating factor instead can be introduced inside the cell or the relevant gene can be located on the episomal unit including the first genic unit (or in any other replicating unit inside the cell), or can be integrated in the genome of the host cell. In any case the gene coding for the activating factor inside the cells of the present invention shall be expressed in order to allow the replication of the first genic unit in the episomal unit.

An example of origin of replication system functional for the present invention, is the relevant system of Epstein-Barr virus (which is the preferred one), wherein the origin of replication is the OriP element and the activating factor is EBNA-1 protein. However also different systems like the one of bovine papilloma virus (BPV) (Calos MP, (1998) Proc Natl Acad Sci USA 95:4084), or those taken from vectors based on SV40 origin-T antigen system, are suitable as well.

The presence of such origin of replication system allows the first genic unit to replicate at low number of copies, while the ITRs in the first genic unit allow the replication at high number of copies in presence of the proteins coded by the E2 regions.

In case instead the first genic unit is integrated in the genome of the host cells, ITRs sequences must be present in head-to-tail configuration in both the extremities of the first unit. Such ITRs in fact enable the rescue and the replication of the first genic unit at high number of copies in presence of the regulatory proteins encoded by the above mentioned genes of E2 regions.

In any case regulatory elements controlling the expression of at least one of the non-structural regions in the first unit, can be further comprised in such a first genic unit or can however be present in the cell, preferably integrated in the cell genome.

An example of such regulatory elements are the elements described by Rittner (Rittner K., et al (1997) J. Virol. 71:3307–3311).

The second genic unit includes an inducible transcription unit which comprises the viral non-structural regions inactivated in the Ad defective genome of the first genic unit, under the control of a strictly regulation-responsive inducible promoter. Such regions can be for example E1, E2 and/or E4.

An inducible promoter in the units object of the present invention, and in particular in the second genic unit, is a promoter induced by an inductor. An example is given by the tetracycline promoter, which is the preferred one, even if promoters regulated by the presence of other inductors like ecdysone, rapamycin, RU486, dexamethasone or heavy metal like Zn or Cd, are suitable as well.

Such a promoter can be operatively linked to regulatory elements like tetracycline-responsive transactivators and/or silencers (rtTA and tTS), both enabling the tight regulation of the transcription unit.

The second genic unit can be introduced in the host cell by a vector which can be viral or plasmidic, can be integrated in the genome of the host cell, or can be present on an episomal unit, in any case must be kept inactive during the growth phase of the cell line to avoid the cytotoxic effect of the viral proteins. At this purpose specific regulatory element enabling the specific repression of said transcription unit can be included in the second genic unit. An example of such a repressor is the Tet/krab fusion protein.

Such repressor elements are in any case functionally coordinated with the inducible promoter and with the regulatory element enhancing the expression of the transcription unit described above.

In absence of the inductor acting on the relevant inducible promoter of the second genic unit (transcription unit) in fact, the non-structural regions contained therein are not expressed, the first genic unit is inactive and there is no production of viral protein toxic for the cell.

For starting the production of the helper dependent adenoviral vector, the helper cell line is infected with the helper dependent adenoviral vector that is to be produced in large amounts, and in the meantime (but also before or after the infection with the defective adenoviral vector) the inductor of the inducible promoters of the second gene unit present in the cell is added, or its expression inside the cell is induced.

The result of such action will be the production of the adenoviral proteins coded by the early regions included in the second genic unit, entailing the activation of the transcriptional cascade of adenoviruses associated to the ITR-mediated replication of the first genic unit.

The consequence of this coordinated series of events is the accumulation of large amounts of structural proteins of the virus, similar to what occurs during the natural infection. The viral proteins are sequestered in the construction of the viral particle and results consequently in the efficient production of the helper-dependent viral vector.

In this connection it shall be pointed out that for the purpose of the present invention an helper dependent adenoviral vector is an Adenoviral vector whose viral cycle cannot be completed in absence of an helper, in particular adenoviral vector wherein the viral genome has been totally or partially deleted with the exception of the packaging signal and the inverted terminal repeats (ITRs). For the purpose of the present invention they are also denominated herein after and before, as helper dependent adenovirus or helper dependent adenovirus virions.

Essentially, this strategy aims at mimicking the phenomenon of the viral latency: in the helper cell a viral genome is kept in a latent phase by suppression of the expression of genes underlying the adenovirus transcriptional cascade. At the moment of the infection/transformation with the defective adenoviral vector that is to be produced, the lytic phase is activated by inducing the expression of the proteins coded by the early genes deleted from the Ad genome included in the first genic unit and put under tight transcription control in the second genic unit.

The previously latent adenoviral genome included in the first unit enters therefore in active replication and transcription, but only the helper dependent vector that is to be produced is packaged, as it only possesses an functional encapsidation signal.

As a consequence of the fact that the system object of the present invention include two instead of three elements, the helper dependent adenoviral vectors production is greatly facilitated, enabling, after a large scale preparation, a final yield of titer levels between $10^9$ and $10^{12}$ particle/millimeter. Such a property of the cell lines of the present invention is particularly relevant if applied in large scale productions like the one of the pharmaceutical industry. Accordingly the present invention enable an improved production of the vectors transferring therapeutical genes suitable in the treatment of human or veterinary diseases.

In any case, it has to be noted that the two genic element can be inserted in the cell in different times. Accordingly the cell lines containing at least the first genic element only, and cell lines containing at least the second genic element only, are a further object of the present invention. The second element in the first case and the first element in the second case, can in fact be added, before or contemporarily the transfection of the cell by the helper dependent adenoviral vector.

In connection with the subject matter disclosed above and below object of the present invention are therefore the cells useful in the production of helper dependent adenoviral vectors, characterised in that they include at least one of the following genic units:

a first genic unit comprising an Adenovirus defective genome having the inverted terminal repeats sequences in head-to-tail configuration, and having both the encapsidation signal and at least one of the non-structural regions, inactivated;

a second genic units comprising at least one inducible promoter and at least one of the regions inactivated in the first genic unit, said regions being under the control of said inducible promoter;

whereby following the activation of the inducible promoter of the second genic unit and the infection of the cell with said helper dependent adenoviral vectors, the first genic unit and the second genic unit enable the production of said helper dependent defective adenoviral in said cells in absence of helper.

Further objects of the present invention are the cells above described wherein the first genic unit is integrated in the genome and the ITRs are present on the both extremities of said first unit in head-tail configuration; the cells above described wherein the first genic unit is comprised in an episomal unit including an element enabling the replication of said genic unit in a low number of copies. In the latter, particular cases are given by cells wherein said element enabling the replication of the episomal unit is, or is derived by, the origin of replication of the origin of replication system of a virus; the case wherein the relevant activating factor is introduced inside the cell from outside the cell; the cases wherein the gene coding for the activating factor is on the episomal unit or in other transcriptional unit inside the cell, or alternatively is integrated in host cell genome.

The origin of replication system described above can be the one of the Epstein-Barr virus (EBV) and the origin of the replication element is OriP and the activating factor is EBNA-1.

Further particular cases referred to each case above are the following: the case wherein the encapsidation signal and/or the non-structural regions of the first genic unit are totally or partially deleted; the case wherein the regions inactivated in the first genic unit and present in the second genic unit is at least one of the early regions selected from the group consisting of E1, E2 and E4 regions, more particularly the case wherein said regions are E1 and E4, the case wherein said regions are E1 E4 and E2A, the case wherein said regions are E1 E4 and E2b polymerase, and the case wherein said regions are E1 E4 and E2b preterminal protein (PTP).

Further cases are the ones wherein the viral region present in the first genic unit is operatively linked to at least one regulatory element enabling the tight control of it's expression; cells in which particularly the promoter on the second genic unit is the tetracycline operator, the promoters regulated by steroid hormones receptors, the promoter regulated by ecdysone receptor, the promoter regulated by rapamycin, the promoter regulated by RU486, and the metallothioneine promoter regulated by metal ions; in these case the relevant inductors are constituted by tetracycline, ecdysone, rapamycin, dexamethasone RU486 and a heavy metal like Zn or Cd respectively; cells in which the viral regions in the second genic unit are operatively linked to elements controlling the expression of the non-structural regions present thereon, and in particular the instance in which such elements is tetracycline-responsive transactivators and/or silencers; the cell which at least one of the non-structural regions in the second genic unit are totally or partially derived from adenovirus genome, preferably human adenovirus, preferably AD2 or AD5 serotype adenoviruses. In these latter cases, the different part of the non-structural regions present on the second genic unit can be derived from adenoviruses of the same serotype or from adenoviruses of a different serotype.

Further cases of interest are constituted by the cells in which the adenovirus genome the first genic unit is derived totally or partially from adenovirus genome of mammalian adenoviruses, preferably human adenoviruses preferably AD2 and AD5 serotype adenovirus. In these latter cases, the different part of the adenovirus genome present on the first ge nic unit can be derived from adenoviruses of the same serotype or from adenoviruses of a different serotype.

The genic units of the present invention can be introduced in the cells in at least one vector, preferably plasmid, kept or not in episomal phase; both in case they are integrated in the host genome and they are present on a replicating unit inside the cell, such first and second genic units can be operatively linked, to genomic sequences ensuring the expression of the functions encoded by at least one of said units in a regulated manner.

Further object of the present invention are the cells including only the first genic unit and the cells including only the second genic unit.

Further, all the above described cells can be eukaryotic cells, preferably mammalian, preferably of humans, and in this latter case also preferably cells permissive for the Adenovirus replication. In particular A549 cell line (human lung carcinoma ATCC CLL 185) are suitable for the derivation of the cells of the present invention.

A further object of the present invention is a method for the production of the above-mentioned cells comprising the following steps:

a) introduction in a cell line of the first genic unit as described above;

b) introduction in the cell line of step a) of second genic unit as described above.

Particular cases are represented by such a method wherein the first genic unit of step a) and the second genic unit of the step b) are introduced in a vector plasmidic or viral. With specific regard to the plasmidic vectors suitable for the present invention cloning vectors like pUC, pBluescript and pLitmus, are to be considered.

With specific regard to the viral vectors suitable for the present invention, retroviral vectors, adeno associated virus vectors, herpes simplex vectors and Epstein-Barr virus derived vectors are to be considered.

Even such methods can be carried out, preferably, on a eukaryotic cell line of mammalians, preferably on a human cell line and preferably on the A549 cell line (human lung carcinoma ATCC CLL 185).

Another object of the present invention is the use of the above-mentioned cells for the production of helper dependent adenoviral vectors, or the A549 cell line (human lung carcinoma ATCC CLL 185) both in vivo and in vitro.

A further object of the present invention is the use of the above-mentioned cells for the production of the helper dependent adenoviral vectors, according to the technique known in the art.

Such helper-dependent adenoviral vectors shall contain at least one gene, which can preferably be a gene of therapeutical interest, whose products in particular are useful in gene therapy, in particular aimed against human or veterinary illnesses. Particular case are the following the case wherein the helper-dependent adenoviral vectors include at least one gene of interest in genetic engineering processes or in processes for producing transgenic animals, the case wherein the products of the activity of said gene are peptides or ribozymes.

A further object of the present invention are also compositions comprising the helper dependent adenoviral vectors, in particular mammalian helper dependent adenoviral vectors, and a vehicle or a carrier, characterised in that said composition is from 99% to 100% free of contaminating helper viruses.

Compositions comprising a vehicle or a carrier and at least one of the cells described above, in particular the cases wherein the cells contain the first genic unit and/or the second genic unit or the case wherein the cells contain the first and the second genic units and the helper-dependent adenoviral vector, are object of the present invention. Such vehicle or carrier can be water, glycerol, ethanol, saline, or the like or the combinations thereof.

Particularly relevant cases are those wherein the vehicle or the carrier in all of these compositions are pharmaceutically acceptable and compatible with the active principle constituted by the above mentioned helper dependent adenoviral vector and/or at least one of the cells above described.

Pharmaceutically acceptable carriers are the ones well known in the art, i.e. sterile aqueous solutions which can contain the active principle only or can further include buffer such as sodium phosphate at physiological pH value, and/or physiological saline such as phosphate buffered saline. In addition, other excipients like a wetting or emulsifying agent, dissolution promoting agent, pH buffering agent, stabilizers and colorants, or the like of any of them, or any other additive known in the art are further included in such compositions.

In this connection pharmaceutically acceptable or compatible carriers or vehicles are referred to the materials known in the art capable of administration to or unto a subject, for example a mammal particularly a human being, without the production of undesirable physiological effect. An example of such effects is given by nausea, gastric upset, dizziness and the like.

The preparation of such compositions, which can be pharmaceutical or pharmacological compositions wherein the active principles are dissolved or dispersed therein, is well understood in the art. Generally such compositions are prepared for parenteral administration or in any case as injectable compositions, either as liquid solutions or suspension. In any case solid forms suitable for solutions or suspension in liquid prior to use can be prepared. Preparations suitable for other desired routes of administration according to the technique well known in the art, like oral route, dermal patches, suppositories, or even also preparation emulsified, are included in the present invention.

Particular cases are provided by the compositions containing the helper-dependent adenoviral vector, or at least one of the cells of the present invention including helper-dependent adenoviral vectors, comprising at least one gene coding for molecules of therapeutical interest, molecules which can be also peptides or ribozymes, in particular useful in gene therapy, more specifically aimed against human illnesses.

Object of the present invention is therefore also the use of the cells object of the present invention as a medicament and in particular for the preparation of the above mentioned compositions, in particular for the pharmaceutical or pharmacological compositions suitable in gene therapy.

A further object of the present invention is the process for the production of at least one of the compositions described above, that can be pharmaceutical compositions or matter compositions.

Further object of the present invention are kits comprising at least one of the compositions described above for the production of the helper dependent adenoviral vectors according to the present invention in vitro, in vivo o ex vivo. Of particular interest are the kit including:

a composition comprising at least one of the cells described above including first genic unit the second genic unit and a helper dependent adenoviral vector;
a composition comprising an inductor capable of activating the inducible promoter in the second genic unit;

Of particular interest is also the case wherein the kit includes:

a composition comprising at least one of the cells described above including the first genic unit and the second genic unit;
a composition comprising at least one helper dependent adenoviral vector including at least an etherologous gene, in particular of therapeutic interest; and optionally
a composition comprising an inductor capable of activating the inducible promoter in the second genic unit.

The kit of the present invention can be kit for the therapeutic use (production in vivo or ex vivo of the helper dependent adenoviral vector comprising at least an gene of therapeutic interest, in particular in gene therapy) and kit for the production in vitro of helper dependent adenoviral vector containing at least one gene, preferably of therapeutic interest.

The invention will be better described with the aid of the annexed figures.

A) Chart of the AD5 shuttle vector (first genic unit): Ad5ΔΨΔE1/E4 represents the genome of a human adenovirus, complete except for deletion of the E1, E4 regions and of the one including the encapsidation signal (Ψ); AdITRs the Ad5 ITRs genic sequences in head-tail configuration; Hygro$^r$ the hygromicyn resistance gene; Amp$^r$ the ampicillyn resistance gene; EBNA-1 the viral transactivator of the Epstein-Barr virus (EBV); and OriP represents the origin of latent replication of the EBV virus.

B) Chart of the E1/E4 vector (second genic unit): where E1 and E4 represent DNA sequences corresponding to E1 and E4 adenovirus regions, MSC I and II are sequences including Multiple Cloning Sites, PminCMV are the minimal promoters of Citomegalovirus (CMV), TRE (Tetracycline Responsive Element) represents seven repeated sequences of the operator of the E. Coli tetracycline resistance gene; β-globin polyA is the polyadenilation site of the β-globin; ColElori is the E. Coli replication origin; SV40 polyA is the SV40 virus polyadenilation site.

C) Chart of the pTet-On/Off vector (regulatory element): where Pcmv and Psv40 are the promoters of CMV and SV40 respectively, (r)tTa indicates the controllable transactivator of tetracycline (or thee inverted one, i.e., the one activated only by a tetracycline). This transactivator in turn consists of the gene coding for the tetracycline repressor (or its mutant rtetR of opposite function) fused to the VP16AD domain of the herpes simplex virus. Neo$^r$ represents the neomycin resistance gene.

D) Chart of the pTet-KRAB vector (regulatory element): essentially similar to the pTet-On/Off vector where the sequences coding for VP16AD domain of the herpes simplex virus are substituted with those of the KRAB domain of the Kox human gene.

Figure 2:
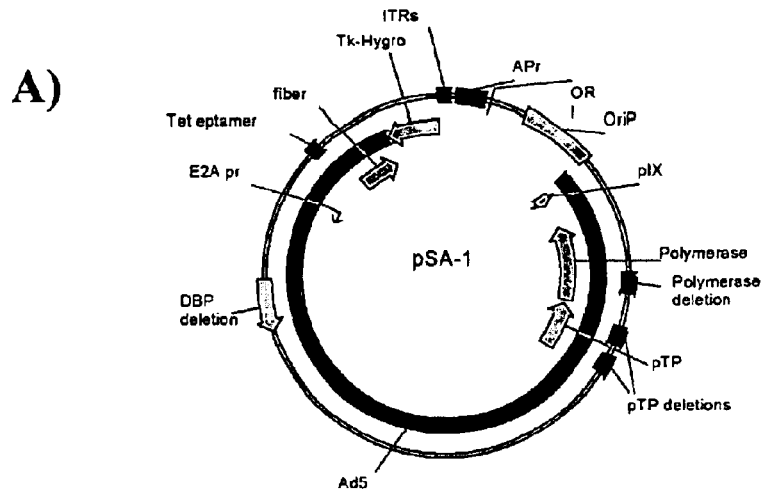
Figure 2:
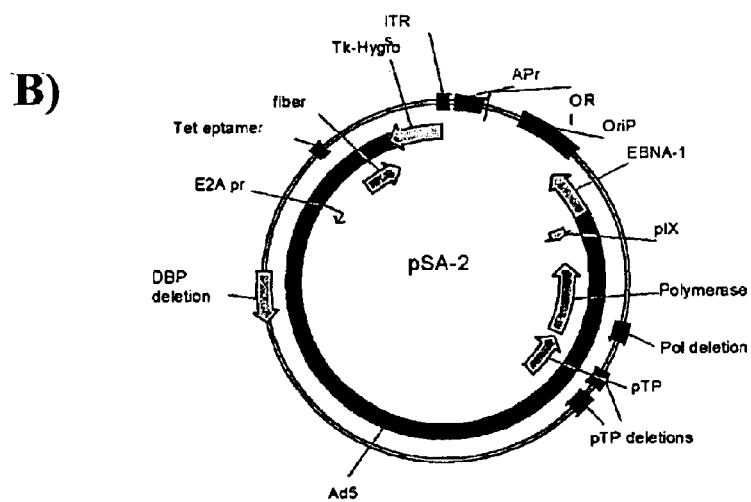
Figure 2:
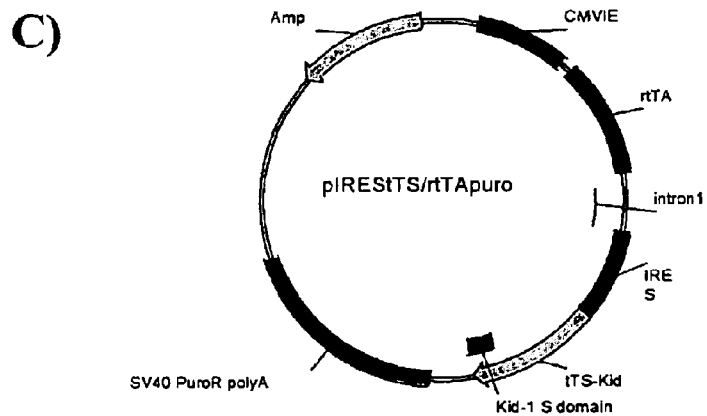

FIG. 2 shows the schematic charts of vectors useful for deriving the helper cell lines of the present invention:

A) Chart of the AD/EBV shuttle vector pSA-1 (first genic unit): Ad5 represents the genome of a human adenovirus, complete except for deletion of the E1, E4 regions and of the one including the encapsidation signal (Ψ); AdITRs the Ad5 ITRs genic sequences in head-tail configuration; Hygro$^r$ the hygromicyn resistance gene; Amp$^r$ the ampicillyn resistance gene; OriP represents the origin of latent replication of the EBV virus; Tet eptamer represent an eptamer of tetracycline repressor DNA binding sites. The sequences of DNA that were deleted to generate different ΔE2 version of this vector are also indicated: DBP deletion represent the deletion of the entire coding sequence of the DNA binding protein; Polymerase deletion represent the deletion of 608 bp within the amino terminus of the polymerase gene; pTP deletion represent the deletion of two DNA segment within the main exon of preterminal protein gene.

B) Chart of the AD/EBV shuttle vector pSA-2 (first genic unit), the only element that differentiate pSA-2 from pSA-1 is the insertion of EBNA-1 gene beside OriP replication origin.

C) Chart of the pIREStTS/rtTApuro (regulatory element) where CMV IE represent human cytomegalovirus immediate early promoter; rtTA represent DNA sequences corresponding Tetracycline reverse transactivator; IRES is the sequence including ribosome internal entry site; tTS Kid represent the sequence corresponding to fusion between tet repressor an silencing domain of Kid-1; Kid-1 S domain is the silencing domain of Kid-1; SV40 PuroR polyA represent the puromycin resistance gene expression cassette; Amp is the ampicillin resistance gene.

DETAILED DESCRIPTION OF THE INVENTION

A first aspect of the present invention is the one referred to the construction and use of the first genic unit as described in the summary of the invention for the derivation of the helper cells of the present invention.

The first genic unit can be constructed as plasmid vector adopting the standard recombinant DNA techniques. Modification (insertions, deletions, mutation) of the first genic unit can obtained according to the procedure described by A. F. Stuart and coworkers (Zhang et al. Nat. Genet. 1998; 20:123–128).

The first unit, when inserted in the genome of the host cell, typically includes:
  i) an adenovirus genome, complete except for the deletion of at least one of the non-structural regions that are essential for the progress of Adenoviral transcriptional cascade and of the one including the encapsidation signal;
  ii) two sequences of Ad inverted terminal repeats (ITRs) in head-to-tail configuration flanking the Adenoviral genome; and generally also
  iii) a marker of selection, like G418 resistance gene, Hygromycyn B resistance gene, puromycin resistance gene, bleomycin resistance gene is present that can be used to select cell line that stably maintain the unit.

Cell lines containing the first genic unit integrated into the host chromosome can be obtained by transformation of the cell with the vector DNA using standard DNA technique and cultivating the transformed-cells in a selective medium (+G418 or Hygromycin B or bleomycin or puromycin), according to the relevant techniques known in the art.

Transcription and replication of an adenoviral vector inserted in the host chromosome between two ITR junctions in head-to-tail configuration can be also activated supplying in trans viral factors deleted and/or the viral functions inactivated from the adenoviral genome using DNA transfection or infection with viral vectors or direct delivery of active viral polypetides.

In the case instead, wherein the first genic unit is kept on an episomal unit the vector used for the introduction of the first unit has been denominated "shuttle vector" such a shuttle vector being a vector (plasmidic or viral) in an episomal form, and has been constructed in order to include the element reported in the point i) above, generally the element reported in the point iii) above and further comprising:
  iv) the origin of the latent replication of a virus and in particular the Epstein-Barr virus (EBV);
  v) the Ad inverted terminal repeats (ITRs) genic sequences in head-tail configuration;

The vector in this case has been denominated "Ad/EBV shuttle vector" due to the characterizing presence of the EBV elements. In a further embodiment in fact also the gene coding for the protein EBNA-1 is included.

In a preferred embodiment of such vector the adenovirus genome of the point i) is deleted of E1 and E4 gene and E2 promoter basal activity is reduced by inserting a Tet silencer binding site into the viral chromosome upstream E2 promoter. In a second preferred embodiment of such vector the adenovirus genome is deleted of E1 and E4 gene and E2a genes. In a third preferred embodiment of such vector the adenovirus genome is deleted of E1 and E4 gene and E2b genes.

An essential characteristic of such a "shuttle vector" is the replicating capacity that reproduces a high number of copies per cell once the transcription of the Ad genes has been activated. This is made possible by the presence in the construct of the inverted terminal repeats (ITRs) of adenovirus in head-tail configuration.

In a preferred embodiment of such vector, the Ad genome is that of the Ad5 serotype, in a second preferred embodiment such vector includes the Ad2 serotype genome. Combinations with other serotype genomes or any other member of the Adenoviridae family are possible, and might be preferred in some applications.

In a preferred embodiment of such vector the ITRs are those of the Ad5 serotype. In a further preferred embodiment of such vector the ITRs are those of the Ad2 serotype. Combinations with ITRs of other serotypes or any other member of the Adenoviridae family are possible and might be preferred in some applications.

Eukariotic cells can be transformed with the first genic unit according to transfection protocols like calcium phosphate method or lipofection or using DNA microinjection. Cells containing the first unit can be selected exploiting the presence on the episome of a selection marker by adding the corresponding antibiotic to the culture medium. Permissive cells containing the first genic unit in episomal form can support the propagation of an adenoviral vector, in presence of the viral functions which have been deleted or inactivated from the Ad defective genome present in the first genic unit.

A cell line obtained as described above, can be used to insert the second genic unit in which the adenoviral function inactivated in the first genic unit are under tight transcriptional control.

The second genic unit can be obtained according to standard recombinant DNA techniques like direct cloning into vectors of DNA fragments obtained by DNA digestion with restriction enzymes, PCR or by homologous recombination technique in E. coli or eukaryotic cells.

The relevant vectors used for the introduction of the second genic unit contains, accordingly, as characterising elements:
  I) the non-structural regions inactivated in the adenoviral genome of the first unit, integrated in the genome of the host cell or present into a "shuttle vector";
  II) an inducible promoter that be strictly regulable; and optionally,
  III) two dimer of insulator sequences flanking the transcriptional unit;
  IV) regulatory elements such tetracycline-responsive elements.

An essential characteristic of such vector is the capacity of being maintained strictly inactive during the growth step of the cell line, in order to avoid the cytotoxic effect of the viral proteins.

In a preferred embodiment of such vector the Ad regions are those of the Ad5 serotype, in a second preferred embodiment of such vector the Ad regions are those of the Ad2 serotype. Combinations with Ad regions of other serotypes or any other member of the Adenoviridae family are possible and might be preferred in some applications.

In a preferred embodiment of such vector the inducible promoter consists of an element responding to tetracycline. The regulation of the expression is in this case based on the use of the two regulatory elements tetracycline-controlled reverse transactivator (rtTA) (Gossen, D. et al. (1995) Science 268:1766–1769) and hybrid transcriptional repressor Tet-KRAB (Deuschle, U. et al. (1995) Mol. Cell. Biol. 15:1907–1914) modified so as to prevent the formation of a rtTA/Tet-KRAB dimer (Freundlieb S., et al. J. Gene Med. 1999; 1:1–13).

Preferably, the use of a vector containing a single tetracycline-responsive element in form of bidirectional expression is provided, such that the basal activity be strictly repressed by the TetR-KRAB repressor. In absence of Doxycycline the TetR-KRAB repressor binds strongly to the tetracycline-responsive element, ensuring a drastic decrease of the basal promoter activity. In presence of Doxycycline, transcription is activated by detachment of Tet-KRAB repressor and by the binding of the rtTA activator to the promoter.

Alternatively, the system can be based on a reverse silencer obtained fusing the KRAB domain responsible for the transcriptional repression and the DNA binding domain of rtTA in combination with the direct transactivator tTA. In this second version of the regulation system, the transcriptional repression takes place cultivating the cells in absence of tetracycline.

Other regulation systems are described in the art, as for instance those based on the use of ligands other than tetracycline like RU486 (Wang, K. E., et al. (1994) PNAS, 91:8180–8184), ecdysone (No, D. et al. (1996) PNAS 93:3346–3351), rapamycine (Spencer, D. M. et al. (1993) Science 262:1019–1024) and their use can easily be adapted to the present invention. For the purpose of the present invention, any genic expression regulator whatsoever may be utilised, as long as it ensures a sufficient regulation and be inducible by use of factors acceptable in the pharmacological practice.

The presence of the two DNA insulator dimers, improve the stability of the second genic unit allowing the inducibility thereof. These DNA elements can be derived from chicken β-globin locus and are known to protect a transcriptional unit from constitutive inactivation due to DNA methylation and negative or positive influences derived by the position of insertion in host chromosome.

In another embodiment of the cell of the present invention contain a second genic unit in a stable form wherein the non-structural regions deleted or in any way inactivated in the Ad genome of the first genic unit present in the "shuttle vector" is operably linked to sequences, preferably genomic, inducibility regulating the expression thereof.

The second genic unit can be contained in one or more vectors and inserted into the cells by transfection techniques, microinjection etc.

A marker of selection, like G418 resistance gene, Hygromycyn B resistance gene, puromycin resistance gene, bleomycin resistance gene is generally present in both the units and can be used to select cell-line that stably maintain one or both of said units, in this latter case both starting from a cell containing one of the unit or stating from a cells containing no one of said units, in any case according to the well know technique in the art.

The cell lines obtained after transformation with the second genic unit are characterized by the possibility to express the non structural regions contained therein in a tight controlled fashion. In the case of regulation of non-structural regions using the Tet system, the addition of tetracycline to the culture medium result in a derepression of tet promoter mediated by Tetracycline-induced dissociation of tTS from TetR DNA binding site followed by a full transcription activation due to rtTa binding.

In the preferred embodiments this cell line includes in a stable form one or more vectors comprising the genes coding for the E1 and E4 or E1, E2 and E4, can complement Ad regions deleted from the "Ad/EBV shuttle vector", of a human Ad virus as described in the second aspect of the present invention. In a preferred embodiment the viral genes are those of the Ad5 serotype and the expression regulation system is based on the use of both the tetracycline-controlled reverse transactivator (rtTA) and of the Tet-KRAB hybrid transcriptional repressor as above-disclosed. However, genetic sequences derived from any other member of Adenovidae family can be used. In its preferred embodiments, this cell line is preferably the A549 line (human Lung carcinoma, ATCC CLL185) as described in the art, however other cell lines permissive for the adenovirus replication are foreseen in the present invention.

In any of the above described cases the derivation of the helper cell line is carried out on eukaryotic cell line, preferably mammalian, preferably of human origin containing the first genic unit included in a stable episomal form a vector (denominated "shuttle plasmid") as above-disclosed in the first aspect of the present invention.

In its preferred embodiments this cell line is preferably the A549 line (human Lung carcinoma, ATCC CLL185) as it is described in the art, but other cell lines of human origin or not, is included in the scope of the present invention, as long as they are permissive for the adenovirus replication.

The helper cell lines so obtained have been used in a method for the production of adenovirus-derived and helper-dependent vectors, which is characterised by the following steps:

a') cultivation of the aforesaid helper cell line, under conditions apt to decrease expression of genes encoded by the adenovirus regions contained inside said cell, said conditions being the condition known in the art for each promoter herein described, as for example the conditions described in the examples. When Tet system is used for the transcriptional control, the cell line will be cultivated in absence of tetracycline;

b') insertion in said helper cell line of the genomic DNA for a helper-dependent adenovirus by vector DNA transfection or infecting the cell as described (Parks, R. J., L. Chen, M. Anton, U. Sankar, M. A. Rudnicki, and F. L. Graham (1996). Proc. Natl. Acad. Sci. USA 93:13656–13570).

c') induction of the expression of the genes encoded by the adenovirus regions contained inside said cell. In the case of Tet controlled transcription by adding doxycycline to the culture-medium.

A large scale production of a fully-deleted HD adenoviral vector is obtained by serial passaging the vector as already described for first generation vectors (Hitt M. M. et al.1995. Meth. Mol. Genet. 7, 13–30).

In a preferred embodiment this method is adopted for the production of helper-dependent adenoviral vectors containing genes coding for the expression of polypeptides of therapeutical interest, preferably for use in gene therapy, preferably for use in human gene therapy.

A general description of the present invention has hereto been provided. A more detailed description of some specific embodiments thereof will hereinafter be given with the aid of the following examples, aimed at providing a better understanding of its purposes, characteristics, advantages and operative modes.

EXAMPLE 1

Construction of an E1 and E4 Expression Vectors.

All plasmids can be constructed adopting the standard recombinant DNA techniques.

The E1 region of the adenovirus 5 can be obtained by PCR utilizing the viral genomic DNA as substrate, and it can be inserted into the pBI plasmid (Baron, U. et al. (1995) Nucleic Acids Res, 23 (17) 3605–3606) containing a bidirectional promoter consisting of a single tetracycline-responsive element (TRE) flanked by two cytomegalovirus (CMV) minimal promoters (Clontech) between the restriction sites NotI and SalI, generating the pBI.E1 plasmid. Then pBI.E1 can be modified inserting the DNA coding for the adenovirus E4 region obtained by PCR, between the restriction sites MluI and NheI, thus obtaining the pBI.E1/E4 construct.

EXAMPLE 2

Construction of an E1/E4 Expression Vectors

All plasmids can be constructed adopting the standard recombinant DNA techniques.

Figure 1:
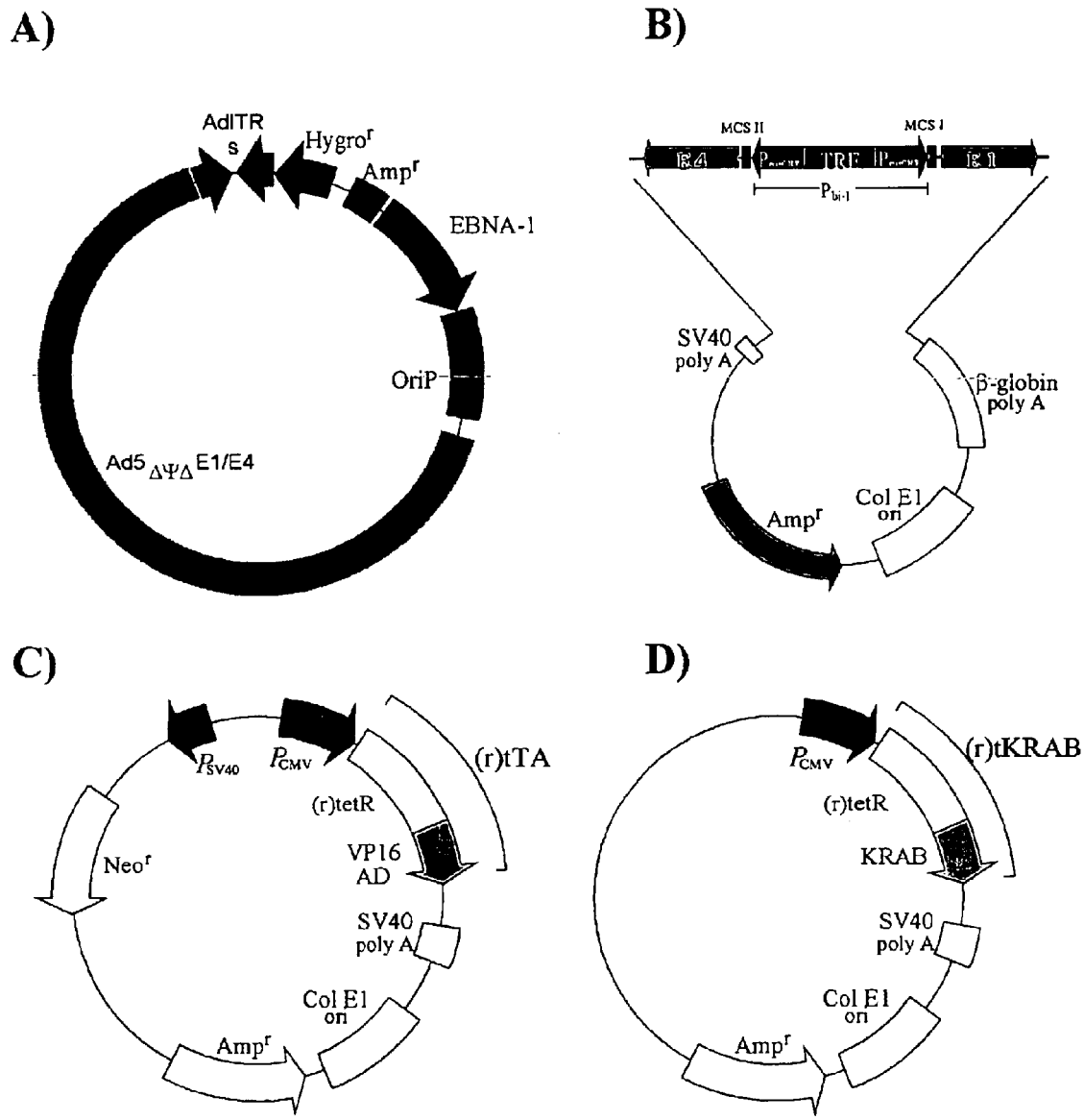
FIG. 1 shows in the four boxes the schematic charts of vectors useful for deriving the helper cell lines of the present invention.

The E4 ORF6 gene DNA was amplified by PCR using the oligonucleotides 5'-TTATACGCGTGCCACCATGACTACGTCCG-3' (SEQ ID NO: 1) and 5'-TTATGCTAGCGCGAAGGAGAAGTCCACG-3' (SEQ ID NO: 2) and pFG140 containing Ad5 viral genomic DNA as substrate. Amplified DNA was inserted into the pBI plasmid (Clontech) (Baron, U. et al. (1995) Nucleic Acids Res, 23 (17) 3605–3606) containing a bidirectional promoter consisting of a single tetracycline-responsive element (TRE) flanked by two cytomegalovirus (CMV) minimal promoters, between the restriction sites MluI and NheI, generating the pBI.E4 plasmid. pBI.E4 was modified by inserting between the restriction sites NotI and SalI, the DNA coding for the adenovirus E1 region obtained by PCR, using the oligonucletides 5'-ATGCGCGGCCGCTGAGTTCCTCAAGAGG-3'(SEQ ID NO: 3) and 5'-ATGCGTCGACCAGTACCTCAATCTGTATCTTC-3' (SEQ ID NO: 4), finally obtaining the pBI.E1/E4 construct (FIG. 1).

Expression vectors for E2a and E2b genes were constructed following the same strategy using plasmid pFG140 to amplify DNA binding protein gene DNA and pVACpol and pVACpTP as templates for polymerase and pre-terminal protein (pTp)cDNA amplification. DBP DNA was cloned into pTRE (Clontech) between restriction sites EcoRI and XbaI. Ad polymerase and pTP were cloned into the same vector or in combination into the bi-directional promoter pBI under Tet operator transcriptional control.

EXAMPLE 3

Construction of a Vector Expressing Tetracycline Controlled Transcriptional Regulators The Tet control system permits regulation of gene activities over a wide range of magnitude in mammalian cell. A transcriptional silencer (tTS) was recently developed by fusing the DNA binding domain of tetracycline repressor with the silencing domain of Kid-1 (Freundlieb S., et al. J. Gene Med. 1999; 1:1–13) tTS and rtTA were combined in a single expression vector as follows. An EcoRI-ClaI DNA fragment containing Tet silencer was isolated from the plasmid pUHS6-1 and inserted downstream the IRES sequence into the vector pIRES-Neo (Clontech) replacing the Neo gene. The new vector pIRES-tTS was modified with the insertion of rtTA gene into the unique EcoRV restriction site downstream the human cytomegalovirus IE promoter, generating pIREStTS/rtTA. In order to introduce a marker of selection to isolate cell clones stably expressing Tet proteins, a puromycin resistance expression cassette obtained from pPUR vector (Clontech) was inserted in the XhoI site of pIREStTS/rtTA generating pIREStTS/rtTApuro (FIG. 2).

EXAMPLE 4

Construction of the Shuttle Plasmid

A 32462 bp DNA fragment containing the whole Adenovirus 5 genome deleted of the E1-region and of the encapsidation signal can be obtained cleaving the plasmid pBHG10 (Bett et al. Proc. Natl. Acad. Sci. 91:8802–8806; 1994) with the restriction enzymes XbaI and ClaI. The resulting fragment can be inserted in the pCEP4 vector (Invitrogen), containing the replication origin of EBV Ori P and the gene for viral transactivator EBNA-1, between the restriction sites SspBI and BamHI, thus obtaining the plasmid pSC. Then the E4 region of the adenovirus genome can be deleted, eliminating the DNA fragment comprised between nucleotides 32810 and 35620, thus generating plasmid pSCΔE4. Subsequently, pSCΔE4 modifications can be inserted in order to optimize the vector characteristics. For instance, the reinsertion into the viral genome of sequences from the Ad5 wt E3 region that have been deleted in the context of pBHG10 can improve the expression levels of the gene encoding the virus fiber. In addition, a DNA fragment including multiple binding sites of the tetracycline repressor (tet-O) can be inserted upstream of the transcription starts of the E2 region in order to further attenuate the residual expression of the adenovirus genome as described by Rittner (Rittner K., et al (1997) J. Virol. 71:3307–33311). In this version of the shuttle plasmid pSCΔE4, its expression is further attenuated by Tet-KRAB, that binds to the E2 region in absence of tetracycline.

EXAMPLE 5

Construction of the Shuttle Plasmid

A: Subcloning and modification of E4 region of Ad5

A DNA fragment containing the whole Adenovirus-5 E4 region was obtained cleaving the plasmid PBHG10 (Bett et al., Proc. Natl. Acad. Sci. 91:8802–8806; 1994) with SpeI and ClaI restriction enzymes. The isolated fragment was ligated in the pBluescript vector (Stratagene), between the restriction sites SpeI and ClaI yielding the plasmid pBSE4. Then pBSE4 was modified by inserting an eptamer of DNA binding sites for the Tet repressor into the unique Pac I restriction site, generating pBSE4-ept. The Tet eptamer DNA was amplified by PCR using the oligonucleotides 5'-CTGATTAATTAAATAGGCGTATCACGAGGCC-3' (SEQ ID NO: 5) and 5'-CTGACGATCGCGTACACGCCTACTC-3' (SEQ ID NO: 6) and the plasmid pUHP10.3 as DNA template. The Tet binding site was cloned into PacI restriction site of pBSE4, just upstream the E2 promoter. The final goal was the reduction of back ground expression of E2 promoter exploiting the silencing effect of tetracycline-controlled transcriptional silencer as described by Rittner (Rittner K., et al (1997) J. Virol. 71:3307–3311). Ad5 E4 region present in PBSE4-ept was then eliminated by digestion with MfeI and ClaI restriction enzymes, the vector DNA was gel-purified and ligated to a Tk-Hygromicyn B resistance expression cassette DNA obtained by PCR with the oligonucleotides 5'-AGTGCACAATTGATTTAAATAATCCGCGCGGTGG-3'(SEQ ID NO: 7) and 5'-TGCAATCGATCAACGCGGGCATCC-3'(SEQ ID NO: 8) using pCEP-4 plasmid DNA template, generating pBSΔE4. The adenovirus ITRs in head-to-tail configuration were than amplified by PCR using the oligonucleotides 5'-TCGAATCGATACGCGAACCTACGC-3'(SEQ ID NO; 9) and 5'-TCGACGTGTCGACTTCGAAGCGCACACCAAAA ACGTC-3'(SEQ ID NO: 10) and pFG140 (Microbix) plasmid DNA as template The Ad ITRs were cloned into the NruI unique site of pBSΔE4, generating pBSΔAE4J.

B: Insertion of EBV OriP into pLBG40

A DNA fragment containing EBV OriP was isolated from pCEP4 vector by MfeI digestion and subcloned into pLitmus 28 (N.E. Biolabs) digested with EcoRI restriction enzyme. The resulting plasmid plit-OriP was then digested with XbaI to release a 2476 bp DNA fragment containing EBV-OriP that was cloned into the unique XbaI site of pLBG40 plasmid (Recchia, A. et al. 1999 Proc. Natl. Acad. Sci. 96:2615–2620) yielding pLBG-OriP.

C: Costruction of Ad/EBV Shuttle Plasmids

A shuttle plasmid pSA-1 (FIG. 2) that carries a copy of Ad5 genome deleted of E1, E3, E4 and packaging signal, was constructed by substituting the DNA fragment of pLBG-OriP comprises between SfuI and PacI restriction sites with the PacI-ClaI DNA fragment derived from pBSΔE4J.

pSA-1 was further modified by inserting EBNA-1 gene as follows. pREP10 (Invitrogen), a plasmid that contain both elements of EBV latent origin of replication, EBNA-1 and OriP, was digested with XbaI and NheI to eliminate a 429-bp DNA fragment containing SV40 polyA. Plasmid DNA was completely filled in, gel-purified and ligated to generate pREP11. pREP11 was then digested with EcoRI and XhoI to release a DNA fragment containing both EBNA-1 gene and OriP. This DNA fragment was subcloned into pLitmus28 digested with EcoRI and XhoI to obtain pREP12. pREP12 was digested with EcoRI and MluI, gel purified and ligated to the 3627 bp EcoRI-MluI DNA fragment isolated from pCEP4, generating pREP13. pREP13 was digested with XbaI and NheT to release a DNA fragment with XbaI-compatible ends that contains EBNA-1 and OriP. Finally, this DNA fragment was cloned into pSA-1. digested with XbaI to generate pSA-2.

EXAMPLE 6

Ad/EBV Shuttle Plasmids Modification

Ad/EBV shuttle plasmids (pSA-1 and pSA-2) were further modified by deleting a DNA sequence corresponding to DNA binding protein (DBP) gene (nucleotides 22443–24032 of Ad5 sequence). The deletion was obtained by homologous recombination in *E. coli*, following the method described by A. F. Stuart and coworkers (Zhang et al. Nat. Genet. 1998;20:123–128). A DNA fragment containing the Tn5 kanamycin resistance gene (neo) flanked by DNA sequences was obtained by PCR with oligonucleotides 5'-GCGGTTAGGCTGTCCTTCTTCTCGACTGACTCC ATGATCTTTTTCTGCCTATAGG AGAAGGAATC-CCGGC GGATTTGTCCTACTCAGGAGAGCG-3' (SEQ ID NO: 11) and 5'-AAATGCTTTTATTTGTACACTCTCGGGTGATTATT TACCCCCACCCTTGCCGTCT GCGCCGTTCTGCAAACCCTATGCTACTCCGTCG-3' (SEQ ID NO: 12) consisting of about 60-bp of homology to DBP gene and, at 3' ends PCR primers to amplify neo gene using pGKfrt as template. Linear DNA containing neo gene was used in recombination experiments to delete the DBP gene from Ad/EBV shuttle plasmids. The same method was applied to construct Ad/EBV shuttle plasmids that do not express Ad polymerase gene and preterminal protein. The sequence of the oligonucleotides used to delete the polymerase gene was 5' -ACGGCCTGGTAGGCGCAGCATCCCTTTTCTACGG GTAGCGCGTATGCCTGCGC GGCCTTCCGGTCTG-CAAACCCTATGCTACTCCGT CG-3' (SEQ ID NO: 13) and 5' -AGACCTATACTTGGATGGGGGCCTTTGGGAAGCA GCTCGTGCCCTTCATGCTG GTCATGTCCCGGCG-GATTTGTCCTACTCAGGAGA GCG-3' (SEQ ID NO: 14). Two pairs of oligonucleotides were used to to delete two regions within the the main exon of pTP:5' -CCGCCTCCCGGTGCGCCGTCGTCGCCGCCGTGT CCCCCCTCCCCCACCGTC CCGGCGGATTTGTCCTACTCAGGAGAGCG-3' (SEQ ID NO: 15) and 5' -GATCTCCGC GTCCGGCTCGTC-CACGGTGGCGGCGAGGTCGTTGGAAATGCGTCTGC a AAACCCTATGCTACTCCGTCG-3' (SEQ ID NO: 16), 5' -TCGACAGAAGCACCATGTCCTTGGGTCCGGCCT GCTGAATGCGCAGGCGTCT GCAAACCCTATGCTACTCCGTCG-3' (SEQ ID NO: 17), and 5' -TCGCCCCGGAGCCCCGGCCACCCTACGCTGGC CCCTCTACCGCCAGCCGCTC CCGGCGGATTTGTCCTACTCAGGAGAGCG-3' (SEQ ID NO: 18). The same method can be applied to other region of Adenovirus genomic DNA relevant to obtain a reduction of cytotoxic effects produced by viral gene expression in the infected cell.

EXAMPLE 7

Evaluation of E1/E4 Expression

In order to assess the regulation of E1 gene expression in cell producing Tet proteins, HeLa cells were seeded on 6-well plates and transfected with pBI.E1/E4 in combination with pIREStTS/rtTApuro. The experiment was done in duplicate with and without doxycycline. 48 hours post-transfection HeLa cells were harvested and cell lysates were analyzed by western blot using a monoclonal antibody directed against E1 proteins. 293 cells that constitutively express E1 region were used as positive control.

A leaky expression of E1 proteins was detectable in cells transfected with pBI.E1/E4 alone. As expected, in presence of Tet regulatory factors, we observed a strong expression of E1 proteins induced by doxycycline, while in absence of drug, the expression was non-detectable. This result demonstrates that the expression of Tet silencer actively repress gene activity, thus abolishing background expression. Simultaneous expression of tTS and rtTA did not affect gene induction via rtTA in presence of doxycycline. This result was confirmed by a second experiment in which HeLa cells were infected with a ΔE1 Ad vector expressing B-galactosidase and then trasfected with pBI.E1/E4 and pIREStTS/rtTApuro. 48 hour post-transfection, HeLa cells were harvested and a lysate was obtained by disrupting the cells freeze and thaw. Monolayers of A549 cells were incubated with aliquot of cell lysate and after 24 hour β-gal activity was detected as described (Parks, R. J. et al 1996; Proc. Natl. Acad. Sci. 91:8802–8806). Since HeLa are not fully permissive for first generation vector replication, no viral progeny was detected in cell that were only infected, while the ΔE1 vector was fully complemented in cell transfected with both vectors (pBI.E1/E4 and pIREStTS/rtTApuro) in presence of doxycycline as demonstrated by the detection of lacz transducing particle in cell lysate. A low β-galactosidase transducing titer was detected after transfection with pBI.E1/E4 as the result of Tet promoter basal activity. On the contrary, no transducing particle were detected in cells maintained in absence of doxycycline after co-transfection of pBI.E1/E4 and pIREStTS/rtTApuro and infected with Ad ΔE1-Bgal. This result confirms that a modulation of E1 gene expression can be obtained combining Tet silencer and rtTA activity. In addition tTS expression represses E1 production below the level necessary to detect viral replication of ΔE1 Ad vector.

EXAMPLE 8

Complementing function of Ad/EBV Shuttle Plasmids

In order to test the Ad helper function of Ad/EBV plasmids, the plasmids were co-transfected into A549EBNA and 293EBNA cell lines in combination with the helper dependent Ad plasmid C4E1E4gfp. This vector contains E1 and E4 adenoviral region as well as green fluorescent protein expression cassette. When both plasmids were introduced in the same cell, the expression of E1 and E4 gene activates Ad/EBV plasmid allowing the replication of both vectors but packaging of C4E1/E4gfp DNA only. Two parallel experiments were performed using both cell lines. 72 hours post-transfection, episomal DNA was extracted from one tissue culture dish according to Hirt method. Transfected cells were harvested from the second dish and disrupted by freeze and thaw to obtain a crude cell lysate. Episomal DNA was digested with HindIII and DpnI restriction enzymes and analyzed by Southern blot. Filters were hybridized with a hygremycyn B DNA probe specific for Ad/EBV plasmid and then, after stripping, re-hybridized with a second DNA probe deriving from C4E1E4gfp that recognizes both plasmids. In parallel, a monolayer of 293 cell was incubated with aliquots of cell lysate to evaluate the production of gfp transducing particles. The results demonstrated that Ad/EBV plasmids replicate in circular form as well as linear form when both Ad (E1/E4) and EBV (EBNA-1) viral transactivator are expressed. In addition, activation of Ad transcriptional program led to C4E1E4gfp DNA replication and packaging into mature virions as demonstrated by the observation of fluorescent gfp expressing cells in the 293 monolayer incubated with cell lysate.

EXAMPLE 9

Construction of a Cell Line Expressing Regulation Proteins

A549 cells (human Lung carcinoma, ATCC CLL185) expressing both the tetracycline-controlled reverse transactivator (Gossen, D. et al. (1995) Science 268:1766–1769) and the Tet-KRAB hybrid transcriptional repressor (Deuschle, U. et al. (1995) Mol. Cell. Biol. 15:1907–1914) can be obtained by cotransfection of the two plasmids pTet-On (Clontech) and pTetKRAB. Subsequently the cell clones obtained by selection with G-418 antibiotic can be tested to evaluate the expression of both transregulating proteins by the use of any vector in which a reporter gene under control of the Tet operator is inserted.

A first generation adenoviral vector was constructed inserting in the Pac I site of the plasmid pLBG40 an expression cassette containing the luciferase gene placed under control of the Tet operator, thus obtaining the plasmid pLBGluc.

This plasmid includes the entire Adenovirus genome deleted of the E1 and E3 regions and therefore it is infective if inserted by transfection in 293 cells. The virus (AdLBGluc) contained in the plaques appearing about 10 days p.t. in 293 cells cultivated in monolayer, was expanded, titrated and assayed for luciferase enzyme expression.

About $10^4$ cells of each clone obtained by resistance to G418 can be seeded in 24-well plates and infected with AdLBGluc virus at a moi of 20. The same number of cells was seeded in duplicate on a second plate and cultivated in presence of doxycycline prior to infection. 48 hours p.i. the cells are harvested and lysated. The expression levels of the luciferase gene were assessed utilizing the natural substrate luciferin. The clones in which the best ratio was observed between the activation of luciferase expression in presence of doxycycline and the basal level in absence of ligand were selected and expanded. A clone prepared according to this procedure was expanded to further define characteristics of growth, stability and expression levels of the regulation proteins. Therefore, suitable banks of frozen cells was prepared to ensure the maintenance of a cell line that express the regulation proteins of the transcription rtTA and Tet-KRAB.

EXAMPLE 10

Construction of the E1/E4-Inducible Cell Line

The plasmid pBI.E1/E4 (see example 1) can be transfected in the cells of the previously selected clone, together with a plasmid expressing resistance to puromycin antibiotic. The cells are selectable by growth on a medium containing the antibiotic and assayed for their expression of adenovirus early proteins under control of tetracycline. For this purpose, a second generation adenoviral vector deleted of both the E1 and of the E4 region can be constructed, as it is described in literature (Brough, D. E. et al. (1996) J. Virol. 70:6497–6501). The cell clones obtained by insertion of the transcriptional unit E1/E4 in the cell can be selected on the basis of their capacity of complementing the helper dependent defective adenoviral vector, thus allowing its replication. Puromycin-resistant clones can be seeded in 24-well plates in duplicate. Then the cells can be infected with the ΔE1/E4 virus and then cultivated with and without addition of doxycycline to the culture medium. In presence of doxycycline the E1 and E4 transcription activation can make cells permissive for viral replication, therefore evidencing the entailed cytopathic effect. The clones, in which the AdΔE1/E4 vector can replicate exclusively in presence of doxycycline, can be expanded and further characterized assessing sustainable production of the defective virus.

EXAMPLE 11

Costruction of an EBNA-1 Expressing A549 Cell Line

An A549 cell line expressing EBNA-1 gene was generated by stable transfection of pEB vector (Ramage, A. D. et al. 1997. Gene 197:83–89). pEB was linearized by MluI restriction and transfected into A549 using Fugene 6 reagent (Boehringer) 72 hours post-transfection A549 cells were split at 1:20 ratio in selective medium containing 600 μg/ml of G418. 10 resistant clones were expanded and tested for episomal replication of plasmid pCEP-EBNAdel containing EBV Ori-P and Hygromycin resistance gene expression cassette.

EXAMPLE 12

Construction of the Helper Cell Line

The shuttle plasmid pSCEΔ4 can be inserted by transfection techniques in the cell line including the E1/E4 inducible transcriptional unit. The resistant cell clones obtained cultivating the transfected cells in presence of the antibiotic hygromicin B can be expanded and further characterized for their capacity to inducibly express the adenovirus genes and to sustain the propagation of an Ad helper-dependent vector. Firstly, the inducible expression of the adenoviral genome can be monitored, assessing the entailed cytopatic effect by cultivating the cells in presence of tetracycline. The production of the adenovirus structural proteins can be quantitatively determined by western blotting and immunoprecipitation techniques with specific antibodies as already described in literature. The capacity of the cell clones including the episome pSCΔE4 of allowing replication of helper-dependent vectors can be studied utilizing different vectors containing the reporter genes coding for the Green Fluorescent Protein (GFP) or for the β-galactosidase or any other gene having an easily detectable activity. The cells can be infected with different moi of the helper-dependent virus, then harvested when the cytopathic effect is evident, after tetracycline-induced expression of the adenoviral genome. The virus yield can be determined using the cellular lysate as described by Parks in PNAS 1996. The assessment of the ratio between the number of transducing viral particles produced infecting the packaging cell lines and those present in the viral inoculum used can allow an evaluation of the virus production efficiency in the different clones obtained.

EXAMPLE 13

Costruction of Cell Lines Containing Ad/EBV Shuttle Vector

A. A549-EBNA Clones containing Ad/EBV Shuttle Vector

Ad/EBV shuttle plasmid was introduced into A549-EBNA cell line using Fugene-6 transfection reagent (Boehringer) or calcium phosphate method. Ad/EBV plasmid was transfected alone or in combination with pIREStTS/rtTApuro or pUHS6-1. The co-transfection of Ad/EBV shuttle vector with plasmids expressing the Tet silencer should further reduce leaking of Ad gene expression by repressing E2 promoter. A549-EBNA cells were put into selective medium containing 400 μg/ml of G-418 and 200 μg/ml of Hygromycin-B 48–72 post-transfection. Isolated Hygromycin-B resistant clones were trasnferred into 24-well plates and expanded.

In order to test A549 Ad/EBV clones for capacity to complement and propagate a helper dependent Ad vector, a new plasmid C4E1E4gfp was constructed. This helper dependent plasmid contains E1 and E4 adenoviral region as well as green fluorescent protein expression cassette. HDC4E1E4gfp vector was rescued and amplified using 293CRE4 cells as described (Parks, R. J. et al. 1996 Proc. Natl. Acad. Sci. 93:13565–13570). A purified preparation of HDC4E1E4gfp was used to infect A549 Ad/EBV clones at low multiplicity of infection.

Clones isolated after Ad/EBV co-transfection with pIREStTS/rtTApuro or pUHS6-1 were tested in duplicate with/out 1 μg/ml of doxycycline. Expression of E1 and E4 genes allowed activation of Ad transcriptional program only in clones containing an intact copy of Ad/EBV shuttle plasmid. The result was the induction of cytopathic effect (cpe) and HD vector propagation.

B. Construction of Different Cell Lines containing Ad/EBV Shuttle VectorII pSA-2 incorporates EBNA-1 expression cassette thus is able to replicate in any cell line permissive for episome maintainance mediated by EBV latent origin of replication. It was then utilized to identify new cell lines different from A549EBNA with improved biological properties. A number of different cell line were transfected and hygromycin B resistant clones were isolated and examined as previously described for clones derived from A549EBNA cells.

EXAMPLE 14

Isolation of a Cell Clone Expressing E1 and E4 Proteins in a Tet Regulated Fashion A549EBNA cells expressing both the tetracycline-controlled reverse transactivator (Gossen, D. et al. (1995) Science 268:1766–1769) and the tTS transcriptional silencer (Deuschle, U. et al. (1995) Mol. Cell. Biol. 15:1907–1914; Freundlieb S., et al. J. Gene Med. 1999; 1:1–13) was obtained transfection of pIREStTS/rtTApuro. Subsequently the cell clones obtained by selection with puromycin antibiotic were tested to evaluate the expression of both trans-regulating proteins by the use of any vector in which a reporter gene under control of the Tet operator is inserted.

A first generation adenoviral vector was constructed inserting in the XbaI site of the plasmid pLBG40 an expression cassette containing the luciferase gene placed under control of the Tet operator,That was obtained by PvuII digestion of pABS-Tetluc, thus obtaining the plasmid pLB-GTetluc.

This plasmid includes the entire Adenovirus genome deleted of the E1 and E3 regions and therefore it is infective when transfected in 293 cells. Isolated plaques were visible 10 days after 293 transfection. Three plaques were picked and analyzed by Hind III digestion following the method described by Graham, F. L. and co-workers 1995, Methods in Molecular Genetics 7:13–30. All three plaques showed the correct restriction pattern. One viral isolate was expanded, titrated and assayed for luciferase enzyme expression.

About $10^4$ cells of each clone obtained by resistance to puromicyn were seeded in duplicate in 24-well plates and infected with AdLBGluc virus at a moi of 20. One plate was cultivated in presence of doxycycline prior to infection. The cells were harvested 48 hours p.i. and lysated. The expression levels of the luciferase gene were assessed utilizing the natural substrate luciferin. The clones in which the best ratio is observed between the activation of luciferase expression in presence of doxycycline and the basal level in absence of ligand were selected and expanded. A clone prepared according to this procedure was expanded to further define characteristics of growth, stability and expression levels of the regulation proteins. Therefore, suitable banks of frozen cells was prepared to ensure the maintenance of a cell line that express the regulation proteins of the transcription rtTA and Tet-KRAB.

EXAMPLE 15

Construction of the E1/E4-Inducible Cell Line

The plasmid pBI.E1/E4 (see example 1) was transfected in the A549EBNA cells together with pIREStTS/rtTApuro. The cells were selected by growth on a medium containing the antibiotic and assayed for their expression of adenovirus early proteins under control of tetracycline. For this purpose, a second generation adenoviral vector deleted of both the E1 and of the E4 region (Krougliak, V. et al 1995 Hum. Gene Ther. 6:1575–1586) was obtained from F. L. Graham and used to screen for positive clones. The cell clones obtained by insertion of the transcriptional unit E1/E4 in the cell were selected on the basis of their capacity of complementing the helper dependent defective adenoviral vector, thus allowing its replication. Puromycin-resistant clones were seeded in 24 well plates in duplicate. Then the cells were infected with the ΔE1/E4 virus and then cultivated with and without addition of doxycycline to the culture medium. In presence of doxycycline the E1 and E4 transcription activation can make cells permissive for viral replication, therefore evidencing the entailed cytopathic effect. Viral titers were evaluated by PCR using the TaqMam method. The clones, in which the AdΔE1/E4 vector can replicate exclusively in presence of doxycycline, were expanded and further characterized assessing sustainable production of the defective virus. The same procedure was followed to obtain A549EBNA clones expressing E2 genes under tetracycline control. The clones obtained were screened using Ad vectors deleted of the corresponding E2 genes.

EXAMPLE 16

Construction of the Helper Cell Lineand HD Propagation

The shuttle plasmid pSA-1 was inserted by standard transfection techniques in the cell line including the E1/E4 inducible transcriptional unit and Tet proteins. Several resistant clones were obtained by splitting the cells 48 hours post-transfection and cultivating it in a selective medium containing also Hygromycin B at a concentration of 200 μg/ml. Resistant clones were expanded and further characterized for their capacity to inducibly express the adenovirus genes and to sustain the propagation of an Ad helper-dependent vector. Firstly, the inducible expression of the adenoviral genome was monitored, assessing the entailed cytopathic effect by cultivating the cells in presence of tetracycline. The induction of the adenovirus structural protein production was quantitatively determined by western blotting and immunoprecipitation techniques with specific antibodies. The capacity of the cell clones including the episome pSA-1 of allowing replication of helper-dependent vectors was studied utilising different vectors containing the reporter genes coding for the Green Fluorescent Protein (GFP) or for the β-galactosidase or any other gene having an easily detectable activity. The cells were infected with different moi of the helper-dependent virus, then harvested when the cytopatic effect is evident, after tetracycline-induced expression of the adenoviral genome. The virus yield was determined using the cellular lysate to infect 293 cell monolayer. The assessment of the ratio between the number of transducing viral particles produced infecting the packaging cell lines and those present in the viral inoculum was used to evaluate the virus production efficiency in the different clones obtained.

The same procedure was followed to derive packaging cell lines with the modified versions of Ad/EBV shuttle plasmid combining different deletion of early genes including E2 genes.

REFERENCES

Baron, U. et al. (1995) Nucleic Acids Res, 23 (17) 3605–3606
Brough, D. E. et al. (1996) J. Virol. 70:6497–6501
Bett et al. Proc. Natl. Acad. Sci. 91:8802–8806; 1994
Calos M. P. 1996 Trends Genet 12: 463–466
Calos M. P., (1998) Proc Natl Acad Sci USA 95:4084
Deuschle, U. et al. (1995) Mol. Cell. Biol. 15:1907–1914
Englehardt et al. Proc. Natl Acad Sci. 91:6196–6200; 1994
Freundlieb S., et al. J. Gene Med. 1999; 1:1–13
Gossen, D. et al. (1995) Science 268:1766–1769
Hitt M. M. et al.1995. Meth. Mol. Genet. 7, 13–30.
Hitt M. M. et al.1997. Advances in Pharmacol 40, 137–206
Horvitz, "Adenoviridae and their replication" in Virology, Field and Knipe, ed. Raven Press, NY; 1990; pages 1679–1740
Kozarsky et al. J. Biol. Chem. 269:1–8; 1994
Krougliak, V. et al 1995 Hum. Gene Ther. 6:1575–1586
No, D. et al. (1996) PNAS 93:3346–3351
Parks, R. J., L. Chen, M. Anton, U. Sankar, M. A. Rudnicki, and F. L. Graham (1996). Proc. Natl. Acad. Sci. USA 93:13656–13570.
Sambrook J. Frtsch E. F. and Maniatis T. (1989)Cold Spring Harbor Laboratory Press, Cold Spring Harbor, N.Y.
Spencer, D. M. et al. (1993) Science 262:1019–1024
Wang, K. E., et al. (1994) PNAS, 91:8180–8184
Yang et al. Proc. Natl Acad. Sci. 91:4407–4411; 1994

What is claimed is:

1. Cells for the production of human helper dependent adenoviral vectors, including at least the following genic units:
   a first genic unit comprising a human adenovirus defective genome having the inverted terminal repeats in head-to-tail configuration, the encapsidation signal inactivated, and at least one of the non-structural regions inactivated;
   a second genic unit comprising at least one inducible promoter and at least one of the regions inactivated in the first genic unit, said regions being under the control of said inducible promoter;
   whereby following the activation of the inducible promoter of the second genic unit and the infection of the cells with said helper dependent adenoviral vectors, the first genic unit and the second genic unit enable the production of said helper dependent adenoviral vectors in said cells in absence of helper vector.

2. Cells according to claim 1, wherein the first genic unit is integrated in the genome of the cells and has at both the extremities inverted terminal repeats in head-to-tail configuration.

3. Cells according to claim 1, wherein the first genic unit is included in an episomal unit including an element enabling the replication of said episomal unit in a low number of copies.

4. Cells according to claim 3, wherein said element enabling the replication of said episomal unit is the origin of replication of a virus.

5. Cells according to claim 4, wherein the gene coding for an activating factor of said origin of replication is further included in the episomal unit.

6. Cells according to claim 4, wherein the gene coding for an activating factor of said origin of replication is integrated in the genome.

7. Cells according to claim 4, wherein said virus is Epstein-Barr virus, the origin of replication is OriP and the activating factor is EBNA-1.

8. Cells according to claim 1, wherein the encapsidation signal of the adenovirus defective genome of the first genic unit is inactivated by total or partial deletion.

9. Cells according to claim 1, wherein the non-structural regions of the adenovirus defective genome of the first genic unit is inactivated by total or partial deletion.

10. Cells according to claim 1, wherein the inactivated regions of the first genic unit are selected from the group consisting of E1, E2A, E2B, and E4.

11. Cells according to claim 10, wherein said regions are E1 and E4.

12. Cells according to claim 10, wherein said regions are E1, E4 and E2A.

13. Cells according to claim 10, wherein said regions are E1, E4 and E2B polymerase.

14. Cells according to claim 10, wherein said regions are E1, E4 and E2B preterminal protein (PTP).

15. Cells according to claim 1 wherein the viral regions of the first genic unit is operatively linked to at least one regulatory element enabling the tight control of the expression of said regions.

16. Cells according to claim 1 wherein the promoter on the second genic unit is the tetracycline operator.

17. Cells according to claim 1 wherein the viral regions in the second genic unit are operatively linked to elements regulating the expression of said regions.

18. Cells according to claim 1, wherein said adenovirus defective genome of the first genic unit is totally or partially derived from a human adenovirus selected from the group consisting of Ad2 and Ad5.

19. Cells according to claim 1, wherein said viral regions of genic unit are totally or partially derived from a human adenovirus selected from the group consisting of Ad2 and Ad5.

20. The cells according to claim 1, wherein said cells are mammalian cells.

21. The cells according to claim 20, wherein said mammalian cells are human cells.

22. Compositions comprising the cell of claim 1, a vehicle or a carrier, characterized in that said composition is free of contaminating helper viruses.

* * * * *

SEQUENCE LISTING

<160> NUMBER OF SEQ ID NOS: 18

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttatacgcgt gccaccatga ctacgtccg                                    29

<210> SEQ ID NO 2
<211> LENGTH: 28
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 2
ttatgctagc gcgaaggaga agtccacg                                          28

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atgcgcggcc gctgagttcc tcaagagg                                          28

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atgcgtcgac cagtacctca atctgtatct tc                                     32

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctgattaatt aaataggcgt atcacgaggc c                                      31

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctgacgatcg cgtacacgcc tactc                                             25

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
agtgcacaat tgatttaaat aatccgcgcg gtgg                                   34

<210> SEQ ID NO 8
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 8
tgcaatcgat caacgcgggc atcc                                              24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tcgaatcgat acgcgaacct acgc                                              24

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tcgacgtgtc gacttcgaag cgcacaccaa aaacgtc                                37

<210> SEQ ID NO 11
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcggttaggc tgtccttctt ctcgactgac tccatgatct ttttctgcct ataggagaag        60
gaatcccggc ggatttgtcc tactcaggag agcg                                   94

<210> SEQ ID NO 12
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaatgctttt atttgtacac tctcgggtga ttatttaccc ccaccttgc cgtctgcgcc         60 gttctgcaaa ccctatgcta ctccgtcg                                          88

<210> SEQ ID NO 13
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
acggcctggt aggcgcagca tccctttttct acgggtagcg cgtatgcctg cgcggccttc      60
cggtctgcaa accctatgct actccgtcg                                         89
```

```
<210> SEQ ID NO 14
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agacctatac ttggatgggg gcctttggga agcagctcgt gcccttcatg ctggtcatgt      60
cccggcggat ttgtcctact caggagagcg                                      90

<210> SEQ ID NO 15
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccgcctcccg gtgcgccgtc gtcgccgccg tgtccccccct ccccaccgt cccggcggat      60 ttgtcctact caggagagcg                                                 80

<210> SEQ ID NO 16
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gatctccgcg tccggctcgc tccacggtgg cggcgaggtc gttggaaatg cgtctgcaaa      60
ccctatgcta ctccgtcg                                                   78

<210> SEQ ID NO 17
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tcgacagaag caccatgtcc ttgggtccgg cctgctgaat gcgcaggcgg tctgcaaacc      60
ctatgctact ccgtcg                                                     76

<210> SEQ ID NO 18
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 tcgccccgg agccccggcc accctacgct ggcccctcta ccgccagccg ctcccggcgg      60
atttgtccta ctcaggagag cg                                              82
```